United States Patent
Parker

(10) Patent No.: US 9,339,155 B1
(45) Date of Patent: May 17, 2016

(54) PORTABLE URINAL

(71) Applicant: Byrd F. Parker, Richardson, TX (US)

(72) Inventor: Byrd F. Parker, Richardson, TX (US)

( * ) Notice: Subject to any disclaimer, the term of this patent is extended or adjusted under 35 U.S.C. 154(b) by 0 days.

(21) Appl. No.: 14/593,023

(22) Filed: Jan. 9, 2015

Related U.S. Application Data

(60) Provisional application No. 61/985,571, filed on Apr. 29, 2014.

(51) Int. Cl.
  *A47K 11/00* (2006.01)
  *A47K 11/12* (2006.01)

(52) U.S. Cl.
  CPC .................... *A47K 11/12* (2013.01)

(58) Field of Classification Search
  CPC ................ A47K 11/06; A47K 11/12
  USPC .................................. 4/144.1–144.4
  See application file for complete search history.

(56) References Cited

U.S. PATENT DOCUMENTS

| | | | | |
|---|---|---|---|---|
| 105,979 A | * | 8/1870 | Price ........................ | 4/144.1 |
| 1,148,897 A | * | 8/1915 | Hayes ................. | A61J 19/00 4/114.1 |
| 1,440,765 A | * | 1/1923 | Buckley ................... | 4/144.1 |
| 2,600,478 A | * | 6/1952 | Butcher ..................... | 4/144.4 |
| 2,769,982 A | * | 11/1956 | Gossett ..................... | 4/144.1 |
| 3,597,853 A | * | 8/1971 | Kucera ................. | A63F 1/06 434/129 |
| 5,305,473 A | * | 4/1994 | Nakamura ................. | 4/306 |
| 5,822,804 A | * | 10/1998 | Hauflaire ................. | 4/144.1 |
| 5,822,806 A | * | 10/1998 | Kizhnerman ............. | 4/310 |
| 7,416,160 B2 | * | 8/2008 | Cies ................. | B65F 1/1615 220/283 |
| 2006/0174402 A1 | * | 8/2006 | Groot et al. ................ | 4/144.1 |
| 2008/0028503 A1 | * | 2/2008 | Brown ................ | A47K 11/12 4/144.1 |
| 2011/0239356 A1 | * | 10/2011 | Peng ......................... | 4/144.1 |
| 2014/0338110 A1 | * | 11/2014 | Huang ................ | A47K 11/12 4/144.2 |

\* cited by examiner

*Primary Examiner* — Huyen Le
(74) *Attorney, Agent, or Firm* — Kenneth L Tolar

(57) ABSTRACT

A portable urinal includes a hollow shell having an upper end, a lower end and an open front face in communication with an interior chamber. Surrounding a portion of the open front face, near the lower end, is a semispherical lip that forms a urinal receptacle. Depending from the lower end of the shell is a threaded post in fluid communication with the urinal receptacle. A disposal bottle includes an internally threaded neck that mates with the threaded post for collecting urine entering the shell. One or more hooks on the rear surface of the shell releasably grip U-shaped brackets mounted on a bedroom wall. Accordingly, the shell provides a temporary, bedside urinal that is more easily accessible than a remote bathroom.

3 Claims, 2 Drawing Sheets

PORTABLE URINAL

CROSS REFERENCE TO RELATED APPLICATIONS

This application is entitled to the benefit of provisional patent application No. 61/985,571 filed on Apr. 29, 2014, the specification of which is incorporated herein by reference.

BACKGROUND OF THE INVENTION

The present invention relates to a portable urinal that provides a temporary, bedside waste station for those with bladder irregularities.

DESCRIPTION OF THE PRIOR ART

During any given night, a sleeper with certain bladder irregularities must repeatedly awaken and search for a bathroom. The repeated bathroom visits disturb others within the dwelling and interrupt valuable sleep time. While attempting to locate the bathroom or a light switch, the sleeper often collides with surrounding objects, causing pain and injury. In severe cases, the sleeper simply does not reach a bathroom in time to avoid an accident.

Accordingly, there is currently a need for a device that eliminates the burdensome practice of repeatedly accessing a remote bathroom throughout the night. The present invention addresses this need by providing a portable urinal that is easily suspended from a wall to provide a temporary, bedside waste station.

SUMMARY OF THE INVENTION

The present invention relates to a portable urinal comprising a hollow shell having an upper end, a lower end and an open front face in communication with an interior chamber. Surrounding a portion of the open front face, near the lower end, is a semispherical lip that forms a urinal receptacle. Depending from the lower end of the shell is a threaded post in fluid communication with the urinal receptacle. A disposal bottle includes an internally threaded neck that mates with the threaded post for collecting urine as it enters the shell. One or more hooks on the rear surface of the shell releasably grip U-shaped brackets mounted on a bedroom wall. Accordingly, the shell provides a temporary, bedside urinal that is more easily accessible than a remote bathroom.

It is therefore an object of the present invention to provide a portable urinal that provides an accessible, bedside waste station for those with bladder irregularities.

It is another object of the present invention to provide a portable urinal that can be easily and removably attached to a bedroom wall.

Other objects, features and advantages of the present invention will become readily apparent from the following detailed description of the preferred embodiment when considered with the attached drawings and the appended claims.

DESCRIPTION OF THE PREFERRED EMBODIMENT

Figure 1:
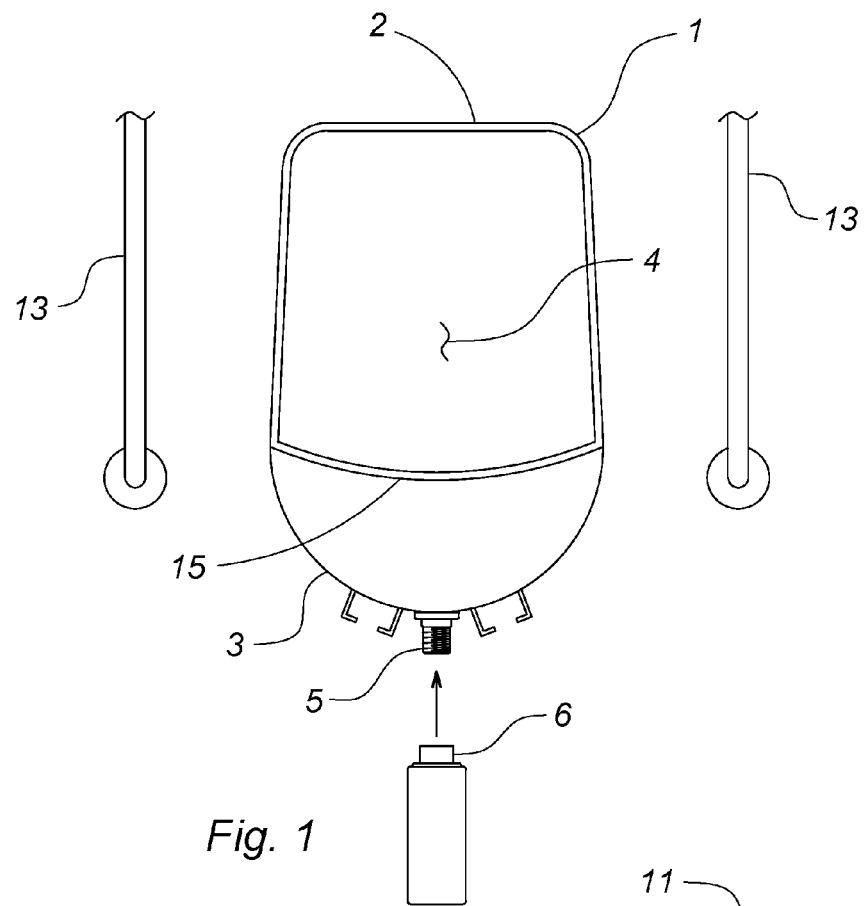
FIG. 1 is a front, plan view of the portable urinal according to the present invention.
Figure 2:
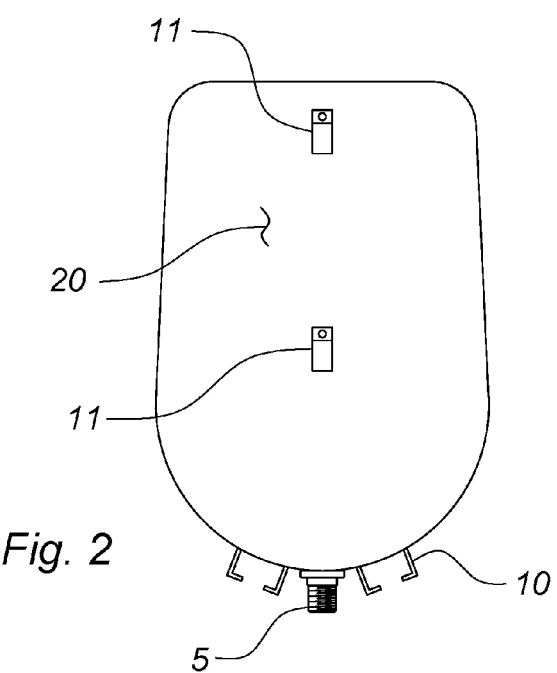
FIG. 2 is a rear, plan view of the urinal.
Figure 3:
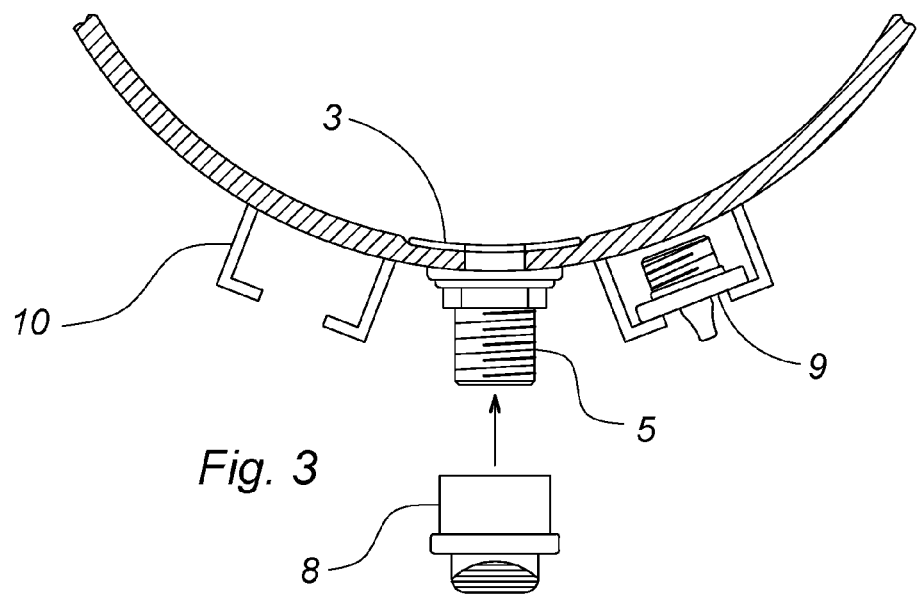
FIG. 3 is a lower, sectional view of the portable urinal.
Figure 5:
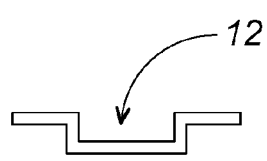
FIG. 5 is an isolated view of an exemplary hook.
Figure 6:
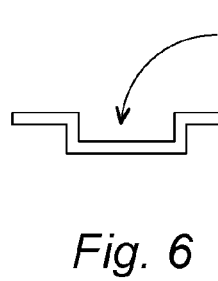
FIG. 6 is an isolated view of an exemplary bracket.
Figure 4:
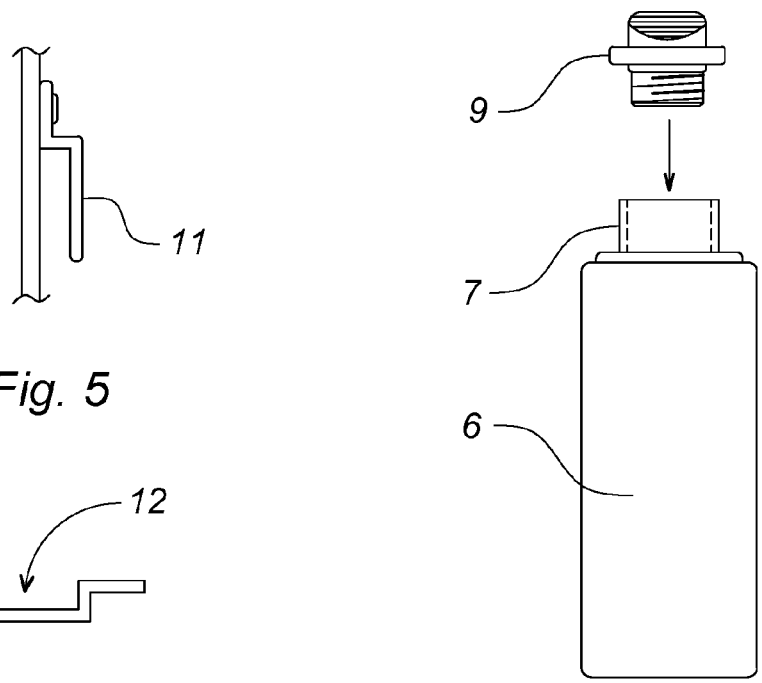
FIG. 4 is an isolated view of the urine disposal bottle.

The present invention relates to a portable urinal comprising a hollow shell 1 having an upper end 2, a lower end 3, a rear surface 20 and an open front face 4 in communication with an interior chamber. Surrounding a portion of the open front face, near the lower end, is a semispherical lip 15 that forms a urinal receptacle. Depending from the lower end of the shell is a threaded post 5 in fluid communication with the urinal receptacle. A disposal bottle 6 includes an internally threaded neck 7 that mates with the threaded post for collecting urine entering the shell.

A cap 8 is configured to mate with the threaded post when the bottle is removed to capture drips from the urinal receptacle. A plug 9 is securable to the threaded neck on the bottle to prevent spills if the bottle is inadvertently dropped or toppled before emptying. On the lower end of the shell are a pair of C-shaped brackets 10 that conveniently retain the cap or plug when not in use.

One or more L-shaped hooks 11 positioned on the rear surface of the shell fit within U-shaped brackets 12 mounted on a bedroom wall. A pair of bars 13 may be mounted adjacent to the shell to assist the sleeper with maintaining balance. Accordingly, the shell provides a temporary, bedside urinal that is more easily accessible than a remote bathroom.

The above-described device is not limited to the exact details of construction and enumeration of parts provided herein. Furthermore, the size, shape and materials of construction of the various components can be varied.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

What is claimed is:
1. A portable urinal comprising:
   a hollow shell having an upper end, a lower end, a rear surface and an open front face in communication with an interior chamber;
   a disposal bottle removably attached to the lower end of the shell and in fluid communication with the interior chamber;
   means for removably attaching the shell to a wall;
   a semispherical lip surrounding a portion of the open front face, near the lower end, said semispherical lip forming a urinal receptacle;
   a threaded post depending from the lower end of the shell, said post in fluid communication with the urinal receptacle;
   said disposal bottle including a threaded neck that mates with the threaded post for collecting urine entering the shell;
   a cap configured to mate with said threaded post when the bottle is removed to contain drips from said urinal receptacle;
   a plug that is securable to the threaded neck on said bottle to prevent spills if said bottle is inadvertently overturned before emptying;
   a pair of C-shaped brackets on the lower end of said shell for retaining said cap and said plug when not in use.

2. The portable urinal according to claim 1 wherein said means for removably attaching the shell to a wall comprises:
- at least one hook on the rear surface of said shell;
- at least one bracket mounted on a bedroom wall for receiving said hook.

3. The portable urinal according to claim 1 further comprising a pair of bars flanking said shell to assist a user with maintaining balance.

\* \* \* \* \*